(12) United States Patent
Watanabe et al.

(10) Patent No.: US 9,943,081 B2
(45) Date of Patent: *Apr. 17, 2018

(54) ANTIBACTERIAL/ANTIVIRAL COATING MATERIAL, AND METHOD FOR FORMING ANTIBACTERIAL/ANTIVIRAL COATING FILM

(71) Applicant: LIXIL CORPORATION, Tokyo (JP)

(72) Inventors: Youichi Watanabe, Tokyo (JP); Yuki Shuto, Tokyo (JP); Yasuhiro Itoda, Tokyo (JP)

(73) Assignee: LIXIL CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/023,940

(22) PCT Filed: Sep. 25, 2014

(86) PCT No.: PCT/JP2014/075514
§ 371 (c)(1),
(2) Date: Mar. 22, 2016

(87) PCT Pub. No.: WO2015/046372
PCT Pub. Date: Apr. 2, 2015

(65) Prior Publication Data
US 2016/0205929 A1 Jul. 21, 2016

(30) Foreign Application Priority Data
Sep. 27, 2013 (JP) .................. 2013-201343

(51) Int. Cl.
| | | |
|---|---|---|
| A01N 33/12 | (2006.01) |
| A01N 37/10 | (2006.01) |
| C09D 5/14 | (2006.01) |
| C09D 7/12 | (2006.01) |
| C09D 133/00 | (2006.01) |

(52) U.S. Cl.
CPC ............ *A01N 33/12* (2013.01); *A01N 37/10* (2013.01); *C09D 5/14* (2013.01); *C09D 7/12* (2013.01); *C09D 7/1216* (2013.01); *C09D 133/00* (2013.01)

(58) Field of Classification Search
CPC ..................................................... A01N 33/12
See application file for complete search history.

(56) References Cited

U.S. PATENT DOCUMENTS

| | | |
|---|---|---|
| 4,847,088 A | 6/1989 | Blank |
| 2005/0215639 A1 | 9/2005 | Mohr et al. |
| 2007/0237901 A1 | 10/2007 | Moses et al. |
| 2010/0115706 A1 | 5/2010 | Bender |

FOREIGN PATENT DOCUMENTS

| | | |
|---|---|---|
| CN | 1431255 A | 7/2003 |
| CN | 1687305 A | 10/2005 |
| CN | 1320079 C | 6/2007 |
| CN | 101394747 A | 3/2009 |
| CN | 101486863 A | 7/2009 |
| CN | 101589189 A | 11/2009 |
| CN | 102505467 A | 6/2012 |
| JP | H01 1265594 A | 10/1989 |
| JP | H01-313408 A | 12/1989 |
| JP | H03-069670 A | 3/1991 |
| JP | 10-265594 A | 10/1998 |
| JP | 2000-191409 A | 7/2000 |
| JP | 2005-527609 A | 9/2005 |
| JP | 2008-189596 A | 8/2008 |
| JP | 2009-055960 A | 3/2009 |
| JP | 2009-528326 A | 8/2009 |
| JP | 2010-195782 A | 9/2010 |
| JP | 2011-058136 A | 3/2011 |
| JP | 2011-072868 A | 4/2011 |
| JP | 2012-071893 A | 4/2012 |
| JP | 2012-176279 A | 9/2012 |

(Continued)

OTHER PUBLICATIONS

Polymer Solutions. Heat Stabilizers: The coolest Polymer Additive. 2015 https://www.polymersolutions.com/blog/heat-stabilizer-analysis/.*
An International Search Report for corresponding International Application No. PCT/JP2014/075513 dated Dec. 9, 2014; 2 pgs.
A Notification of Reasons for Refusal from corresponding JP Patent Application No. 2013-201342 dated Sep. 27, 2016; 6 pgs.
An Office Action from corresponding CN Patent Application No. 201480052469.8 dated Oct. 21, 2016; 19 pgs.
A Notification of Reasons for Refusal from corresponding JP Patent Application No. 2013-201343 dated Nov. 29, 2016; 5 pgs.
An Office Action for U.S. Appl. No. 15/023,921 dated Nov. 30, 2016; 6 pgs.

(Continued)

*Primary Examiner* — Adam C Milligan
*Assistant Examiner* — Sarah Alawadi
(74) *Attorney, Agent, or Firm* — Muncy, Geissler, Olds & Lowe, P.C.

(57) ABSTRACT

An antibacterial/antiviral coating material is provided, which allows for forming a highly water-resistant antibacterial/antiviral coating film. The antibacterial/antiviral coating material is obtained by blending, into an acrylic-melamine resin coating material, a quaternary ammonium salt (A) represented by Formula (1) below, and a polyhydric carboxylic acid (B) having a C6 or more hydrocarbon group and two or more carboxyl groups. (In Formula (1), R1 represents a C8-22 alkyl group; R2A, R2B and R2C each independently represent a C1-3 alkyl group; and X represents a halogen atom).

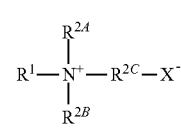

(1)

2 Claims, No Drawings

(56) References Cited

FOREIGN PATENT DOCUMENTS

| JP | 2013-71031 A | 4/2013 |
| JP | 2013-71893 A | 4/2013 |
| JP | 2010-083830 A | 4/2015 |
| WO | WO 2011-089840 A1 | 7/2011 |
| WO | WO 2013/047642 A1 | 4/2013 |
| WO | WO2014/008264 * | 7/2013 |

OTHER PUBLICATIONS

A Notification of Reasons for Refusal from corresponding JP Patent Application No. 2013-201342 dated Dec. 20, 2016; 6 pgs.
An Office Action for CN Patent Application No. 201480052471.5 dated Jan. 17, 2017; 16 pgs.

* cited by examiner

ANTIBACTERIAL/ANTIVIRAL COATING MATERIAL, AND METHOD FOR FORMING ANTIBACTERIAL/ANTIVIRAL COATING FILM

TECHNICAL FIELD

The present invention relates to an antibacterial/antiviral coating material, which allows for forming a highly water-resistant antibacterial/antiviral coating film, and to a method for forming the antibacterial/antiviral coating film using the antibacterial/antiviral coating material. The present invention also relates to an antibacterial/antiviral coating film, which is formed by way of the method for forming an antibacterial/antiviral coating film, and to a member having the antibacterial/antiviral coating film.

BACKGROUND ART

As a technology for forming an antibacterial/antiviral coating film on a construction material, Patent Document 1 proposes a method for forming a surface coating film with paint, to which a quaternary ammonium salt such as alkyltrimethylammonium salt is added. Patent Document 1 also discloses that the durability of the coating film can be enhanced by further blending a coating-film curing accelerator such as p-toluenesulfonate into the coating material for forming the surface coating film.

Patent Document 1: Japanese Unexamined Patent Application, Publication No. 2013-71031

DISCLOSURE OF THE INVENTION

Problems to be Solved by the Invention

In recent years, along with increasing awareness about hygienic and esthetic aspects in a living environment, an antibacterial/antiviral coating film finds application in a wide variety of products. For example, in relation to water supply-and-drainage members such as faucet handles for kitchen sinks and bathrooms, the antibacterial/antiviral effects thereof are required to remain intact even after having been left under a wet condition for a long period of time; in other words, such members are required to have a highly water-resistant antibacterial/antiviral coating film.

The surface coating film of Patent Document 1 is not considered to have sufficient water resistance, and has suffered from the problem of losing the antibacterial/antiviral effects when immersed in water.

An object of the present invention is to provide: an antibacterial/antiviral coating material which allows for forming a highly water-resistant antibacterial/antiviral coating film; a method for forming an antibacterial/antiviral coating film using the antibacterial/antiviral coating material; an antibacterial/antiviral coating film formed by way of the method for forming an antibacterial/antiviral coating film; and a member having the antibacterial/antiviral coating film.

Means for Solving the Problems

The inventors of the present invention have eagerly studied how to solve the problem, and have found that the problem can be solved by combining a particular polyhydric carboxylic acid with a quaternary ammonium salt that serves as an antibacterial component.

The present invention has been made based on such a finding, and is characterized in the following aspects.

A first aspect of the present invention is an antibacterial/antiviral coating material obtained by blending, into an acrylic-melamine resin coating material, a quaternary ammonium salt (A) represented by Formula (1) below, and a polyhydric carboxylic acid (B) having a C6 or more hydrocarbon group and two or more carboxyl groups.

[Chem. 1]

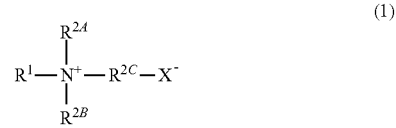

(1)

(In Formula (1), $R^1$ represents a C8-22 alkyl group; $R^{2A}$, $R^{2B}$ and $R^{2C}$ each independently represent a C1-3 alkyl group; and X represents a halogen atom).

A second aspect of the present invention is the antibacterial/antiviral coating material according to the first aspect, in which the quaternary ammonium salt (A) is at least one of octadecyltrimethylammonium chloride and hexadecyltrimethylammonium chloride.

A third aspect of the present invention is the antibacterial/antiviral coating material according to the first or second aspect, in which the polyhydric carboxylic acid (B) is an aromatic polyhydric carboxylic acid.

A fourth aspect of the present invention is the antibacterial/antiviral coating material according to any one of the first to third aspects, in which the antibacterial/antiviral coating material contains 1-10 parts by weight of the quaternary ammonium salt (A) in relation to 100 parts by weight of solid content of the acrylic-melamine resin coating material.

A fifth aspect of the present invention is the antibacterial/antiviral coating material according to any one of the first to fourth aspects, in which the antibacterial/antiviral coating material contains the quaternary ammonium salt (A) and the polyhydric carboxylic acid (B), in a mole ratio represented by, quaternary ammonium salt (A):polyhydric carboxylic acid=1:0.01-0.5.

A sixth aspect of the present invention is a method for forming an antibacterial/antiviral coating film, in which the antibacterial/antiviral coating material according to any one of the first to fifth aspects is attached to a surface to be treated, and is subsequently heat-treated.

A seventh aspect of the present invention is an antibacterial/antiviral coating film formed by way of the method for forming an antibacterial/antiviral coating film according to the sixth aspect.

An eighth aspect of the present invention is a member, on a surface of which the antibacterial/antiviral coating film according to the seventh aspect is formed.

Effects of the Invention

According to the present invention, the quaternary ammonium salt (A) in the antibacterial/antiviral coating material is ionically bonded to the polyhydric carboxylic acid (B), which together form a high-molecular-weight ionically-bonded complex that is stably retained in the antibacterial/antiviral coating film, thereby preventing the quaternary ammonium salt (A) from being eluted in water. Therefore, the antibacterial/antiviral effects of the quaternary ammonium salt (A) are prevented from being deteriorated by elution of the quaternary ammonium salt (A).

Therefore, in application to water supply-and-drainage members such as faucet handles for kitchens and bathrooms as well, a highly durable antibacterial/antiviral coating film can be formed, which allows for maintaining the antibacterial/antiviral effects for a long term.

PREFERRED MODE FOR CARRYING OUT THE INVENTION

The mode for carrying out the present invention is described below in detail.

[Antibacterial/Antiviral Coating Material]

An antibacterial/antiviral coating material of the present invention is obtained by blending, into an acrylic-melamine resin coating material, a quaternary ammonium salt (A) represented by Formula (1) below, and a polyhydric carboxylic acid (B) having a C6 or more hydrocarbon group and two or more carboxyl groups.

[Chem. 2]

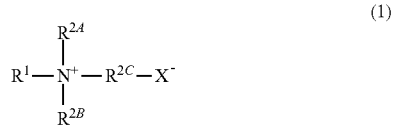

(1)

(In Formula (1), $R^1$ represents a C8-22 alkyl group; $R^{2A}$, $R^{2B}$ and $R^{2C}$ each independently represent a C1-3 alkyl group; and X represents a halogen atom).

<Quaternary Ammonium Salt (A)>

The quaternary ammonium salt (A) functions as an antibacterial component. In Formula (1) above, it is preferable that $R^1$ is a C12-18 alkyl group, a C16-18 alkyl group in particular; and it is preferable that $R^{2A}$, $R^{2B}$ and $R^{2C}$ are a methyl group. Examples of X include a chlorine atom and a bromine atom.

Examples of the quaternary ammonium salt (A) represented by Formula (1) include dodecyltrimethylammonium chloride ($R^1=C_{12}H_{25}$), hexadecyltrimethylammonium chloride ($R^1=C_{16}H_{33}$), octadecyltrimethylammonium chloride ($R^1=C_{18}H_{37}$), etc. Among these, in particular, it is preferable that octadecyltrimethylammonium chloride or hexadecyltrimethylammonium chloride is used, from the perspectives of the antibacterial/antiviral effects and safety.

A single species of the quaternary ammonium salt (A) may be used alone, or two or more species thereof may be used in combination.

<Polyhydric Carboxylic Acid (B)>

A carboxyl group of the polyhydric carboxylic acid (B) is ionically bonded to a quaternary ammonium group of the quaternary ammonium salt (A) being an antibacterial/antiviral component, thereby forming an ionically-bonded complex. In this case, since the polyhydric carboxylic acid (B) has two or more carboxyl groups, two or more quaternary ammonium salts (A) are bonded to a single polyhydric carboxylic acid (B), thereby forming a high-molecular-weight ionically-bonded complex in an antibacterial/antiviral coating film. The high-molecular-weight ionically-bonded complex is not easily eluted from the coating film even when immersed in water, and is stably retained in the antibacterial/antiviral coating film; therefore, the antibacterial/antiviral effects are prevented from being deteriorated through contact with water.

In order to form a high-molecular-weight ionically-bonded complex in this manner, the number of the carboxyl groups of the polyhydric carboxylic acid (B) is required to be two or more. It is preferable that the number of the carboxyl groups of the polyhydric carboxylic acid (B) is about 2 to 4, in particular.

Further, a C5 or lower hydrocarbon group of the polyhydric carboxylic acid (B) cannot form a highly water-resistant antibacterial/antiviral coating film. An upper limit of the carbon number of the hydrocarbon group is not restricted in particular, but is ordinarily 20 or below, from the perspectives of handleability and availability.

It is preferable that the hydrocarbon group of the polyhydric carboxylic acid (B) is an aromatic group, which is capable of forming a structurally stable ionically-bonded complex; and it is preferable that the polyhydric carboxylic acid (B) is an aromatic polyhydric carboxylic acid, in which two or more carboxyl groups are bonded to an aromatic hydrocarbon ring, in particular. Specifically, examples of the aromatic polyhydric carboxylic acid (B) include a pyromellitic acid and a trimesic acid. It is preferable that the aromatic polyhydric carboxylic acid (B) is a trimesic acid.

As in the case of such aromatic polyhydric carboxylic acids, as long as the polyhydric carboxylic acid (B) has the carboxyl groups bonded in a radial direction, since the carboxyl groups are separated from each other, a quaternary ammonium salt (A) can be easily bonded thereto, and a stable high-molecular-weight ionically-bonded complex can be formed.

A single species of the polyhydric carboxylic acid (B) may be used alone, or two or more species thereof may be used in combination.

<Coating Material>

In the present invention, among highly weather-resistant and durable acrylic coating materials, it is preferable that the coating material is an acrylic-melamine resin coating material, from the perspective of balancing the adhesiveness and the antibacterial/antiviral effects.

Note that the acrylic-melamine resin coating material may be any one of a solvent-type coating material or a water-type coating material.

<Content Ratio of Quaternary Ammonium Salt (A) to Polyhydric Carboxylic Acid (B) in the Coating Material>

In the antibacterial/antiviral coating material of the present invention, in order to form a highly water-resistant antibacterial/antiviral coating film, although the blend ratio of the quaternary ammonium salt (A) to the polyhydric carboxylic acid (B) may vary depending on the number of the carboxyl groups of the polyhydric carboxylic acid (B), it is preferable that the blend ratio is: the quaternary ammonium salt (A) to the polyhydric carboxylic acid (B)=1:0.01-0.5, and in particular, 1:0.1-0.2, in a mole ratio of the quaternary ammonium salt (A) to the carboxylic acid (B). If the quaternary ammonium salt (A) is below the range, and the polyhydric carboxylic acid (B) is above the range, the antibacterial/antiviral effects tend to be deteriorated; and conversely, if the quaternary ammonium salt (A) is above the range, and the carboxylic acid (B) is below the range, the effects of enhancing the water resistance in combination with the polyhydric carboxylic acid (B) may not be sufficiently obtained.

Further, in relation to the content of the quaternary ammonium salt (A) in the antibacterial/antiviral coating material, an excessively low content thereof tends to deteriorate the antibacterial/antiviral effects of the antibacterial/antiviral coating film formed, and an excessively high content thereof tends to deteriorate the film performance. Therefore, it is preferable that the content of the quaternary ammonium salt (A) in the antibacterial/antiviral coating material is 1-10 parts by weight, and in particular, 4-6 parts by weight, in relation to 100 parts by weight of the solid content of the acrylic-melamine resin coating material; and it is preferable that the polyhydric carboxylic acid (B) is included in the range described above, in relation to the quaternary ammonium salt (A).

<Other Components>

The antibacterial/antiviral coating material of the present invention may contain a quaternary ammonium salt (A) and a polyhydric carboxylic acid (B) in an acrylic-melamine resin coating material, and may contain, as necessary, other types of antibacterial components, coating-film curing accelerators, colorants, etc., other than the quaternary ammonium salt (A) and the polyhydric carboxylic acid (B). [Method for forming antibacterial/antiviral coating film]

According to a method for forming an antibacterial/antiviral coating film of the present invention, the antibacterial/antiviral coating material of the present invention is attached to a surface to be subjected to antibacterial/antiviral treatment, and is subsequently heat-treated, thereby forming an antibacterial/antiviral coating film.

A method for attaching the antibacterial/antiviral coating material of the present invention to a surface to be treated is not limited in particular; and the method may be a coating method such as brush coating or spray coating, or may be a method, in which an object to be treated is directly immersed in the antibacterial/antiviral coating material of the present invention for a predetermined period of time.

If the heat treatment temperature after attaching the antibacterial/antiviral coating material to the surface to be treated is excessively low, a highly water-resistant antibacterial/antiviral coating film by virtue of the ionic bond between the quaternary ammonium salt (A) and the polyhydric carboxylic acid (B) cannot be formed; and conversely, if the heat treatment temperature is excessively high, the antibacterial/antiviral treatment surface and the treatment object may be thermally deteriorated. Therefore, although the heat treatment temperature may vary depending on the type of the acrylic-melamine resin coating material to be used, the heat treatment temperature is preferably 150-170° C., and is further preferably 155-165° C. Although the heat treatment duration may vary depending on the heat treatment temperature, the heat treatment duration is preferably 20-40 minutes, and is further preferably 25-35 minutes.

Note that, prior to forming an antibacterial/antiviral coating film, a primer layer and a medium coating film, as disclosed in Patent Document 1, may be formed on a surface to be treated, as necessary.

A film thickness of the antibacterial/antiviral coating film of the present invention, which is formed in this manner, is not limited in particular, and may vary depending on the intended use of a member and/or presence or absence of an undercoating layer, to which the antibacterial/antiviral coating film is applied; however, the film thickness is ordinarily about 10-30 μm. If the film thickness is excessively thin, the durability of the coating film may be deteriorated; and if the film thickness is excessively thick, the film may separate, and further there is an economic disadvantage in using a large amount of the coating material.

[Antibacterial/Antiviral Member]

The antibacterial/antiviral coating film of the present invention can be applied to, without any limitation, a wide variety of members such as, for example, interior and exterior building components such as handrails, fixtures, fixture knobs, pulling handles, and grips; parts such as faucet handles for kitchens, wash rooms, bathrooms, toilets, etc.; stationery; other commodities; etc. Further, the substrate thereof can also be a member molded or processed from metal, resin, wood, glass, ceramic, etc.; the molded member may include an extruded material of aluminum or resin, a cast piece of aluminum or iron, and an injection-molded piece of resin; and the processed member may include a press-worked piece, etc. In relation to such applications, because of the high water resistance, the antibacterial/antiviral coating film of the present invention is favorably applied to members which may contact water, such as faucet handles for kitchens, wash rooms, bathrooms, toilets, etc.

EXAMPLES

The present invention is described more specifically by way of the following Examples.

Note that, in the following Examples and Comparative Examples, the antibacterial/antiviral effects were evaluated through the following methods.

<Antibacterial Effects: Measurement of Antibacterial Activity Value>

An antibacterial test was performed in accordance with JIS Z 2801. *Escherichia coli* (NBRC3972) was used as a test target bacteria. Specifically, a test piece (5 cm×5 cm) was put into a sterilized dish; 0.4 mL bacterial suspension for inoculation was inoculated into the test piece; and the top surface of the test piece was covered with a polypropylene film of 4 cm square. This was put into a desiccator, at 35° C. temperature and 90% or higher RH; and after ten minutes of contact, the number of living bacteria was measured by way of the following measuring method. Further, a bacterial suspension for inoculation was inoculated into a control piece being a non-processed film (ABS film) of the same size in substitution for the test piece; and immediately after the inoculation, and after ten minutes of contact, the number of living bacteria was measured by way of the following measuring method, in a manner similar to the test piece.

(Method for Measuring the Number of Living Bacteria)

The polypropylene film and the test piece were put together into a sterilized polyethylene bag for stomacher; 10 mL SCDLP culture medium was added thereto; and the test bacteria were washed out by hand or stomacher. The number of living bacteria in 1 mL of this washout liquid was measured by way of an SCDLP agar medium culture method. The number of living bacteria was converted into a number per 1 $cm^2$ of the test piece.

An antibacterial activity value of each test piece was calculated in accordance with the following equation.

Antibacterial activity value=Logarithmic value of the number of living bacteria in the control piece after ten minutes−Logarithmic value of the number of living bacteria in the test piece after ten minutes Antibacterial activity values of 3.0 or higher were evaluated as the most superior antibacterial effects (A:); antibacterial activity values between 2.0 inclusive and 3.0 exclusive were evaluated as superior antibacterial effects (B); and antibacterial activity values below 2.0 were evaluated as inferior antibacterial effects (C).

<Antiviral Effects: Measurement of Viral Inactivation Rate>

An antiviral test was performed in accordance with an antibacterial test method (JIS Z 2801). A sample was put into a moisture retention dish; 0.2 mL test virus liquid was inoculated into a test piece; the contact efficiency between the test viruses and the test piece was enhanced by covering the top surface with a polypropylene film; and an interaction was carried out at room temperature for 20 minutes. After the interaction, the test piece was put into a styrol case; 10 mL phosphate-buffered physiological saline was added thereto; and it was shaken for three minutes to elicit viruses. This liquid was used as an undiluted solution for a viral infectivity titer measurement sample. The undiluted solution for the viral infectivity titer measurement sample was subjected to 10-fold serial dilution with a phosphate-buffered physiological saline; subsequently, 50 μL of the undiluted solution for the measurement sample or the diluted virus liquid, and 50 μL of Madin-Darby canine kidney (MDCK) cell suspended in Dulbecco's modified Eagle's Medium (DMEM) including 5% fetal bovine serum, were loaded in a 96-well plate; and it was cultured in a carbon dioxide gas incubator for four days. After the incubation, cytopathogenic effects were examined under a microscope; a viral infectivity titer test was performed by way of a Reed-Muench method; and logarithm decrement thereof was calculated as a viral inactivation rate.

Viral inactivation rates of 99% or higher were evaluated as superior antiviral effects (D); and viral inactivation rates below 99% were evaluated as inferior antiviral effects (E).

Examples 1-5, Comparative Examples 1-3, and Reference Example 1

A quaternary ammonium salt shown in Table 1 and a carboxylic acid shown in Table 1 were blended, in each ratio shown in Table 1, into an acrylic-melamine resin coating material ("Magicron 1000", the solvent-type coating material manufactured by Kansai Paint Co., Ltd.) or an acrylic-urethane resin coating material ("Rethan PG80", the acrylic urethane coating material manufactured by Kansai Paint Co., Ltd.) (note that carboxylic acid was not added in Reference Example 1 and Comparative Example 1); the coating material obtained was spray-coated onto a zinc die-casting part; and subsequently, the acrylic-melamine resin coating material was calcined at 160° C. for 30 minutes; and the acrylic-urethane resin coating material was calcined at 80° C. for 30 minutes, thereby forming a coating film with a film thickness of 20 μm.

A water resistance test was carried out by immersing each sample in water of 25° C. for 16 hours; and the antibacterial/antiviral effects were evaluated in the manner described above; the result thereof is shown in Table 1. In Table 1, octadecyltrimethylammonium chloride is abbreviated to "ODTMAC"; and hexadecyltrimethylammonium chloride is abbreviated to "HDTMAC".

Note that Reference Example 1 shows antibacterial/antiviral effects of a sample without performing a water resistance test.

TABLE 1

| | TYPE OF COATING MATERIAL | QUATERNARY AMMONIUM SALT | | CARBOXYLIC ACID | | WATER RESISTANCE TEST |
|---|---|---|---|---|---|---|
| | | SPECIES | AMOUNT OF ADDITION (*1) | SPECIES | AMOUNT OF ADDITION (*2) | |
| REFERENCE EXAMPLE 1 | ACRYLIC-MELAMINE RESIN COATING MATERIAL | ODTMAC | 5 | — | — | — |
| COMPARATIVE EXAMPLE 1 | | | | — | — | 25° C. * 16 HOURS |
| COMPARATIVE EXAMPLE 2 | | | | BENZOIC ACID | 0.18 (0.1) | |
| EXAMPLE 1 | | | | TEREPHTHALIC ACID | 0.24 (0.1) | |
| EXAMPLE 2 | | | | TRIMESIC ACID | 0.30 (0.1) | |
| EXAMPLE 3 | | | | PYROMELLITIC ACID | 0.37 (0.1) | |
| EXAMPLE 4 | | | | TRIMESIC ACID | 1.51 (0.5) | |
| EXAMPLE 5 | | HDTMAC | 5 | TRIMESIC ACID | 0.30 (0.1) | 25° C. * 16 HOURS |
| COMPARATIVE EXAMPLE 3 | ACRYLIC-URETHANE RESIN COATING MATERIAL | ODTMAC | 5 | TRIMESIC ACID | 0.30 (0.1) | 25° C. * 16 HOURS |

| | ANTIBACTERIAL EFFECTS | | ANTIVIRAL EFFECTS | |
|---|---|---|---|---|
| | ANTIBACTERIAL ACTIVITY VALUE | EVALUATION | VIRAL INACTIVATION RATE | EVALUATION |
| REFERENCE EXAMPLE 1 | 4.0 | A | 99.98% | D |
| COMPARATIVE EXAMPLE 1 | 1.8 | C | 68% | E |
| COMPARATIVE EXAMPLE 2 | 1.8 | C | — | — |

TABLE 1-continued

| | | | | |
|---|---|---|---|---|
| EXAMPLE 1 | 2.2 | B | — | — |
| EXAMPLE 2 | 4 | A | 99% | D |
| EXAMPLE 3 | 3 | B | — | — |
| EXAMPLE 4 | 2.5 | B | — | — |
| EXAMPLE 5 | 3 | B | — | — |
| COMPARATIVE EXAMPLE 3 | 0.8 | C | — | — |

(*1). The amount of addition to the solid content of the coating material (% by weight)
(*2). Numerical values in upper part of each cell represent the amount of addition to the solid content of the coating material (% by weight)
Numerical values in parenthesis in lower part of each cell represent a ratio to 1 mol of the quaternary ammonium salt (mole ratio).

As is evident from Table 1, it is understood that the water resistance of the antibacterial/antiviral coating film can be enhanced by using a particular polyhydric carboxylic acid in combination with octadecyltrimethylammonium chloride or hexadecyltrimethylammonium chloride; and that the antibacterial/antiviral effects after the water resistance test are superior in the cases of using a trimesic acid as a polyhydric carboxylic acid, in particular. The result of Example 4 reveals that, if an excessive amount of polyhydric carboxylic acid is added, the antibacterial effects are slightly deteriorated. Further, Comparative Example 3 reveals that the acrylic-melamine resin coating material is preferable to the acrylic-urethane resin coating material, as a coating material.

The invention claimed is:

1. An antibacterial and antiviral coating material obtained by blending, into an acrylic-melamine resin coating material, a quaternary ammonium salt represented by Formula (1) below, and a polyhydric carboxylic acid having a C6 or more hydrocarbon group and two or more carboxyl groups,

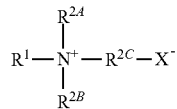

(1)

wherein $R^1$ represents a C8-22 alkyl group; $R^{2A}$, $R^{2B}$, and $R^{2C}$ each independently represents a C1-3 alkyl group; and X represents a halogen atom, wherein the quaternary ammonium salt is present in 1-10 parts by weight in relation to 100 parts by weight of solid content of the acrylic-melamine resin coating material, wherein the quaternary ammonium salt and the polyhydric carboxylic acid are present in a mole ratio represented by quaternary ammonium salt: polyhydric carboxylic acid of 1:0.1-0.2, wherein the quaternary ammonium salt is octadecyltrimethylammonium chloride, and wherein the polyhydric carboxylic acid is trimesic acid.

2. A method for forming an antibacterial and antiviral coating film, wherein the antibacterial and antiviral coating material according to claim 1 is attached to a surface to be treated, and is subsequently heat-treated.

* * * * *